United States Patent [19]

Florio et al.

[11] Patent Number: 5,549,649
[45] Date of Patent: Aug. 27, 1996

[54] PROGRAMMABLE PACEMAKER INCLUDING AN ATRIAL RATE FILTER FOR DERIVING A FILTERED ATRIAL RATE USED FOR SWITCHING PACING MODES

[75] Inventors: Joseph J. Florio, Sunland; Gene A. Bornzin, Camarillo; Paul A. Levine; J. Jeffrey Barlow, both of Newhall, all of Calif.

[73] Assignee: Pacesetter, Inc., Sylmar, Calif.

[21] Appl. No.: 258,014

[22] Filed: Jun. 10, 1994

[51] Int. Cl.$^6$ ........................................ A61N 1/36
[52] U.S. Cl. ............................................... 607/15
[58] Field of Search ................................ 607/9, 14, 15, 607/17, 25

[56] References Cited

U.S. PATENT DOCUMENTS

| | | |
|---|---|---|
| 4,429,697 | 2/1984 | Nappholz et al. . |
| 4,485,818 | 12/1984 | Leckrone et al. . |
| 4,515,161 | 5/1985 | Wittkampf et al. . |
| 4,539,991 | 9/1985 | Boute et al. . |
| 4,554,920 | 11/1985 | Baker, Jr. et al. . |
| 4,624,260 | 11/1986 | Baker, Jr. et al. . |
| 4,712,555 | 12/1987 | Thornander et al. . |
| 4,714,079 | 12/1987 | Hedberg et al. . |
| 4,722,341 | 2/1988 | Hedberg et al. . |
| 4,872,459 | 10/1989 | Pless et al. . |
| 4,880,005 | 11/1989 | Pless et al. . |
| 4,944,298 | 7/1990 | Sholder . |
| 5,085,215 | 2/1992 | Nappholz et al. . |
| 5,133,350 | 7/1992 | Duffin . |
| 5,144,949 | 9/1992 | Olson . |
| 5,161,527 | 11/1992 | Nappholz et al. . |
| 5,282,465 | 2/1994 | van der Veen et al. .................. 607/17 |
| 5,292,340 | 3/1994 | Crosby et al. ............................. 607/17 |

*Primary Examiner*—William E. Kamm
*Assistant Examiner*—Jeffrey R. Jastrzab
*Attorney, Agent, or Firm*—Lisa P. Weinberg

[57] ABSTRACT

An implantable dual-chamber pacemaker programmed to operate primarily in an atrial tracking mode is provided, where the pacemaker includes an atrial rate smoothing filter for producing a filtered atrial rate from an intrinsic atrial rate, and where the pacemaker automatically switches its mode of operation from the atrial tracking mode to a non-atrial tracking mode in the event the filtered atrial rate exceeds a prescribed upper rate limit. The pacemaker switches from a primary set of operational parameter settings for the primary mode, to an alternate set of operational parameters for the alternate mode when the mode is switched from the primary mode to the alternate mode. The pacemaker also includes the capability of recording and storing mode switching events and data pertaining to the mode switching events.

35 Claims, 4 Drawing Sheets

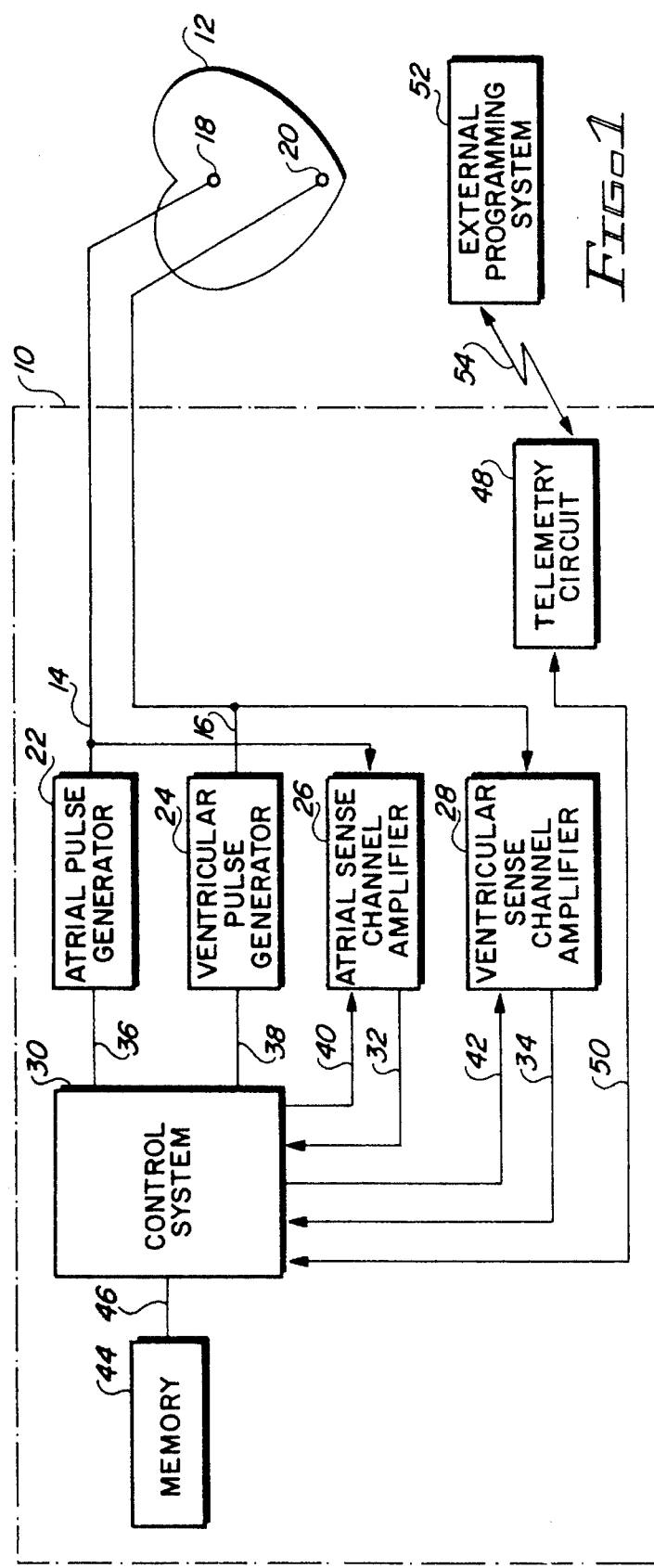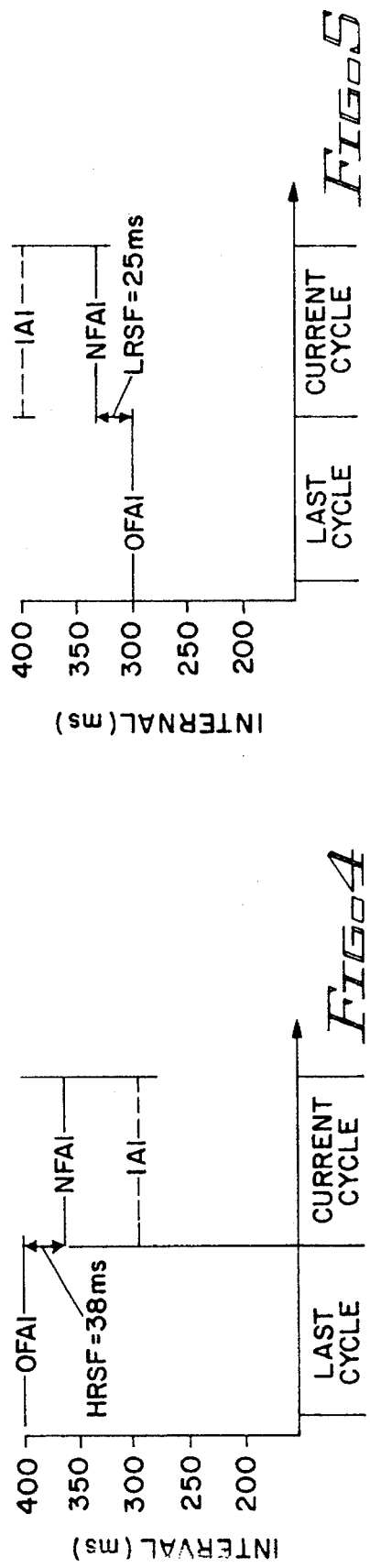

PROGRAMMABLE PACEMAKER INCLUDING AN ATRIAL RATE FILTER FOR DERIVING A FILTERED ATRIAL RATE USED FOR SWITCHING PACING MODES

BACKGROUND OF THE INVENTION

The present invention relates generally to programmable implantable pacemakers, and particularly to dual-chamber pacemakers capable of switching from an atrial tracking mode of operation to a non-atrial tracking mode in response to an occurrence of an atrial arrhythmia. More particularly, the present invention relates to a mode switching pacemaker that includes an atrial rate smoothing filter for producing a filtered atrial rate, where the pacemaker automatically switches its mode of operation from an atrial tracking mode to a non-atrial tracking mode in the event the filtered atrial rate exceeds a prescribed upper rate limit.

Essentially, the heart is a pump which pumps blood throughout the body. It consists of four chambers, two atria and two ventricles. In order for the heart to efficiently perform its function as a pump, the atrial muscles and ventricular muscles should contract in a proper sequence and in a timed relationship.

In a given cardiac cycle (corresponding to one "beat" of the heart), the two atria contract, forcing the blood therein into the ventricles. A short time later, the two ventricles contract, forcing the blood therein to the lungs (from the right ventricle) or through the body (from the left ventricle). Meanwhile, blood from the body fills the right atrium and blood from the lungs fills the left atrium, waiting for the next cycle to begin. A typical healthy adult heart may beat at a rate of 60–70 beats per minute (bpm) while at rest, and may increase its rate to 140–180 bpm when the adult is engaging in strenuous physical exercise, or undergoing other physiologic stress.

The healthy heart controls its rhythm from its SA node, located in the upper portion of the right atrium. The SA node generates an electrical impulse at a rate commonly referred to as the "sinus" or "intrinsic" rate. This impulse is delivered to the atrial tissue when the atria are to contract and, after a suitable delay (on the order of 40–80 milliseconds), propagates to the ventricular tissue when the ventricles are to contract.

When the atria contract, a detectable electrical signal referred to as a P-wave is generated. When the ventricles contract, a detectable electrical signal referred to as an R-wave is generated. The R-wave is much larger than the P-wave, principally because the ventricular muscle tissue is much more massive than the atrial muscle tissue. The atrial muscle tissue need only produce a contraction sufficient to move the blood a very short distance—from the respective atrium to its corresponding ventricle. The ventricular muscle tissue, on the other hand, must produce a contraction sufficient to push the blood over a long distance (e.g., through the complete circulatory system of the entire body).

Other electrical signals or waves are also detectable within a cardiac cycle, such as a Q-wave (which immediately precedes an R-wave), an S-wave (which immediately follows an R-wave), and a T-wave (which represents the repolarization of the ventricular muscle tissue).

It is the function of a pacemaker to provide electrical stimulation pulses to the appropriate chamber(s) of the heart (atria or ventricles) in the event the heart is unable to beat on its own (i.e., in the event either the SA node fails to generate its own natural stimulation pulses at an appropriate sinus rate, or in the event such natural stimulation pulses do not effectively propagate to the appropriate cardiac tissue). Most modern pacemakers accomplish this function by operating in a "demand" mode where stimulation pulses from the pacemaker are provided to the heart only when it is not beating on its own, as sensed by monitoring the appropriate chamber of the heart for the occurrence of a P-wave or an R-wave. If a P-wave or an R-wave is not sensed within a prescribed period of time (which period of time is often referred to as the "escape interval"), then a stimulation pulse is generated at the conclusion of this prescribed period of time and delivered to the appropriate heart chamber via a pacemaker lead.

Modern programmable pacemakers are generally of two types: (1) single-chamber pacemakers, and (2) dual-chamber pacemakers. In a single-chamber pacemaker, the pacemaker provides stimulation pulses to, and senses cardiac activity within, a single-chamber of the heart (e.g., either the right ventricle or the right atrium). In a dual-chamber pacemaker, the pacemaker provides stimulation pulses to, and senses cardiac activity within, two chambers of the heart (e.g., both the right atrium and the right ventricle). The left atrium and left ventricle can also be paced, provided that suitable electrical contacts are made therewith.

In general, both single and dual-chamber pacemakers are classified by type according to a three letter code. In this code, the first letter identifies the chamber of the heart that is paced (i.e., the chamber where a stimulation pulse is delivered)—with a "V" indicating the ventricle, an "A" indicating the atrium, and a "D" indicating both the atrium and ventricle. The second letter of the code identifies the chamber where cardiac activity is sensed, using the same letters to identify the atrium or ventricle or both, and where an "0" indicates that no sensing takes place.

The third letter of the code identifies the action or response that is taken by the pacemaker. In general, three types of action or responses are recognized: (1) an Inhibiting ("I") response, where a stimulation pulse is delivered to the designated chamber after a set period of time unless cardiac activity is sensed during that time, in which case the stimulation pulse is inhibited; (2) a Trigger ("T") response, where a stimulation pulse is delivered to the designated chamber of the heart a prescribed period after a sensed event; or (3) a Dual ("D") response, where both the Inhibiting mode and Trigger mode are evoked, inhibiting in one chamber of the heart and triggering in the other.

A fourth letter, "R" is sometimes added to the code to signify that the particular mode identified by the three letter code is rate-responsive, where the pacing rate may be adjusted automatically by the pacemaker based on one or more physiological factors, such as blood oxygen level or the patient's activity level.

Thus, for example, a DVI pacemaker is a pacemaker that paces in both chambers of the heart, but only senses in the ventricle, and that operates by inhibiting stimulation pulses when prior ventricular activity is sensed. Because it paces in two chambers, it is considered a dual-chamber pacemaker. A VVI pacemaker, on the other hand, is a pacemaker that paces only in the ventricle. Because only one chamber is involved, it is classified as a single-chamber pacemaker. Most dual-chamber pacemakers can also be programmed to operate in a single-chamber mode.

Much has been written and described in the art about the various types of pacemakers and the advantages and disadvantages of each. For example, reference is made to commonly assigned U.S. Pat. No. 4,712,555 of Thornander et al., where some helpful background information about pacemakers and the manner in which they interface with a patient's heart is presented. This patent is hereby incorporated by reference in its entirety.

One of the most versatile programmable pacemakers available today is the DDDR pacemaker. This pacemaker represents a fully automatic pacemaker which is capable of sensing and pacing in both the atrium and ventricle, and is also capable of adjusting the pacing rate based on one or more physiological factors, such as the patient's activity level. When functioning properly, the DDDR pacemaker can limit certain drawbacks associated with the use of pacemakers. For example, the DDDR pacemaker can maintain AV synchrony while providing bradycardia support.

In general, DDDR pacing has four functional states: (1) P-wave sensing, ventricular pacing (PV); (2) atrial pacing, ventricular pacing (AV); (3) P-wave sensing, R-wave sensing (PR); and (4) atrial pacing, R-wave sensing (AR). Advantageously, for the patient with complete or partial heart block, the P state of the DDDR pacemaker tracks the atrial rate which is set by the heart's SA node, and then paces in the ventricle at a rate that follows this atrial rate. Because the rate set by the SA node represents the rate at which the heart should beat in order to meet the physiologic demands of the body (at least for a heart having a properly functioning SA node) the rate maintained in the ventricle by such a pacemaker is truly physiologic.

Those skilled in the art have long recognized the advantages of using an atrial tracking pacemaker. For example, U.S. Pat. No. 4,624,260 to Baker, Jr. et al. discloses a microprocessor controlled dual-chamber pacemaker having conditional atrial tracking capability. Similarly, U.S. Pat. No. 4,485,818 of Leckrone et al. discloses a microprocessor-based pacemaker which may be programmed to operate in one of a plurality of possible operating modes, including an atrial rate tracking mode.

Unfortunately, in some instances, a given patient may develop fast atrial rhythms which result from a pathologic arrhythmia such as a pathological tachycardia, fibrillation or flutter. In these cases, a DDDR pacemaker may pace the ventricle in response to the sensed atrial arrhythmia up to the programmed maximum tracking rate (MTR).

Sometimes it is possible at the time of implantation of a pacemaker to determine whether an atrial fibrillation, atrial flutter, or atrial tachycardia condition is going to develop. In such instances, the pacemaker may always be programmed to operate in a different mode of operation, the leads may be repositioned within the heart, or other actions may be taken to minimize the likelihood of such pathologic arrhythmias occurring. Unfortunately, however, it is not always possible at the time of implantation to determine whether a patient will develop an atrial arrhythmia after the pacemaker is implanted.

Therefore, if such pathologic arrhythmias subsequently occur, they must be treated using other techniques, such as through the administration of drugs. Needless to say, the administration of drugs normally requires the attendance of a physician. Unfortunately, however, a physician is not always present when such pathologic arrhythmias develop, and even when a physician is available, such drugs also may undesirably suppress the ability of the SA node to increase the sinus rate during periods of exercise, emotional stress, or other physiologic stress. Thus, the use of such drugs may prevent the pacemaker from functioning as a intrinsic physiologic rate-responsive pacemaker.

As a result, attempts have been made in the art to prevent undesirable tracking of pathologic atrial arrhythmias by automatically switching the pacemaker's mode of operation from an atrial tracking pacing mode to a non-atrial tracking pacing mode. For example, U.S. Pat. No. 4,722,341 of Hedberg et al., teaches an atrium-controlled pacemaker, where the pacemaker temporarily switches from an atrial tracking mode to a non-atrial tracking mode for a fixed number of stimulation pulses if the sensed atrial activity indicates an atrial arrhythmia may be developing. Unfortunately, however, for some patients, a temporary switching from one mode to another without the capability of remaining in the secondary mode for an extended period of time may not be sufficient to correct or arrest the arrhythmia.

In addition, some previously known mode switching techniques are based in whole or in part on the patient's sensed atrial rate exceeding the MTR. This mode switching criterion may cause problems for patients who exhibit normal sinus tachycardia due to physical activity. Another difficulty associated with previously known techniques is that mode switching occasionally occurred due to electrical noise present in the atrial sensing channel of the pacemaker, or due to a one-of-a-kind fast P-wave. In the above instances, rates slightly exceeding the MTR are not indicative of a pathologic arrhythmia. These patients may thus be subjected to undesirably frequent mode switching occurrences as their atrial rates slightly exceed and then drop below the MTR.

This problem was addressed in commonly assigned U.S. Pat. No. 4,944,928 of Sholder, which is hereby incorporated by reference in its entirety. The '928 patent discloses an atrial tracking pacemaker with automatic mode switching capability. The pacemaker's features include the capability of setting a tachycardia rate limit (TRL) slightly above the MTR, so that mode switching to a non-atrial tracking mode occurs when the TRL is exceeded. A third threshold rate is also set at a value below the MTR. The pacemaker switches back to an atrial tracking mode when the patient's atrial rate drops below this third threshold. To avoid mode switching based on a single short atrial interval between atrial events, the atrial rate is continuously averaged over several cycles. This technique effectively prevents frequent mode switches in patients whose atrial rates "hover" around the MTR.

The techniques discussed in the '928 patent represent significant advances over previously known mode switching techniques. However, some concerns remain unaddressed. For example, certain patients may exhibit atrial rates that drastically fluctuate over short periods of time. In such patients, the sensed atrial rate, and even the averaged atrial rate, may frequently exceed the MTR as well as the TRL, and thus result in frequent mode switching even if no pathologic arrhythmia is occurring. In addition, the averaged atrial rate may be distorted if one or more false signals (e.g., electrical noise) are interpreted as atrial events. Finally, for active patients exhibiting a normal sinus tachycardia, a return to the atrial tracking mode set at a threshold rate lower than the MTR may be inappropriate.

Thus, it would be desirable for the pacemaker to switch the pacing mode from an atrial tracking mode to an non-atrial tracking mode only if a pathologic arrhythmia is detected. It would also be desirable to avoid repetitive mode switching based on fluctuations in the sensed atrial rate.

A pacemaker usually has a number of operational parameters which control the pacemaker's performance. Examples of operational parameters include, but are not limited to, the base rate, the AV delay, the atrial and ventricular refractory periods, and the atrial and ventricular sensing configurations. These parameters are typically set initially by the pacemaker manufacturer, but may be changed by a medical practitioner at the time of implantation or during the patient's follow-up visits.

In a typical previously known pacemaker, a mode switch entails changing the primary mode pacing, sensing, and response configurations of the pacemaker to the alternate mode configurations. For example, the primary mode may be DDD, where the pacemaker paces and senses in both the atrial and ventricular chambers, while inhibiting pacing pulses in one chamber and triggering pacing pulses in the other. An alternate mode may be VVI, where the pacemaker paces, senses, and inhibits pacing pulses only in the ventricle. However, since operational parameters are typically defined only for the pacemaker's primary mode of operation, the operational parameters of the pacemaker remain the same after a switch to the alternate mode. This may be undesirable since certain operational parameter settings may cause the pacemaker to perform in a less than optimal manner in the alternate mode, because the settings are usually optimized for performance in the primary mode. Thus, it would be desirable for the pacemaker to have the capability of switching to a different set of operational parameters associated with the alternate pacing mode when the pacemaker switches to the alternate mode, in order to optimize the performance of the pacemaker during the alternate mode.

When initially configuring the pacemaker, the medical practitioner may set the criteria for mode switching, define the primary mode, and select the alternate mode appropriate for the patient. Pacemaker configuration is typically performed soon after the pacemaker is implanted using an implantable device programmer. After implantation, the medical practitioner typically performs periodic follow-up examinations to determine if the pacemaker is operating properly. During these examinations, the medical practitioner can make adjustments to the operational parameters of the pacemaker, and may also adjust the mode switching criteria to improve the performance of the pacemaker. However, it may be difficult to determine if the pacemaker was performing as desired under the previous mode switching criteria. Often the medical practitioner is forced to rely on the patient's description of discomfort to make the determination that the mode switching criteria need to be adjusted. Thus, it would be desirable if the pacemaker could record mode switching events and data pertaining to the mode switching events (e.g., the duration of the switch, the atrial rate at the time of switch, etc.), and store the event and associated data in pacemaker memory for retrieval by the medical practitioner during a follow-up examination.

SUMMARY OF THE INVENTION

The disadvantages and limitations discussed above are overcome by the present invention. In accordance with this invention, an implantable dual-chamber pacemaker programmed to operate primarily in an atrial tracking mode is provided, where the pacemaker includes an atrial rate smoothing filter for producing a filtered atrial rate from an intrinsic atrial rate, and where the pacemaker automatically switches its mode of operation from the atrial tracking mode to a non-atrial tracking mode in the event the filtered atrial rate exceeds a prescribed upper rate limit.

The pacemaker of the present invention includes a control system for controlling the operation of the pacemaker, a set of leads for receiving atrial and ventricular signals and for delivering atrial and ventricular stimulation pulses, a set of amplifiers for amplifying the atrial and ventricular signals, and pulse generators for generating atrial and ventricular stimulation pulses. In addition, the pacemaker includes memory for storing operational parameters for the control system and for storing data acquired by the control system for later retrieval by the medical practitioner using an external programmer. The pacemaker also includes a telemetry circuit for communicating with the external programmer.

Unlike previously known mode switching pacemakers which switch pacing modes based on an intrinsic or averaged atrial rate, the pacemaker of the present invention uses a filtered atrial rate (FAR) as a basis for mode switching in order to reduce mode switching responses due to, for example, electrical noise or one-of-a-kind fast P-waves. The pacemaker of the present invention obtains the FAR by filtering the intrinsic atrial rate using a rate smoothing filter.

The rate smoothing filter produces the FAR during each cycle by limiting the amount by which the FAR may change from cycle to cycle. This is accomplished by increasing the FAR by a programmable high rate factor when the intrinsic atrial rate increases, and by decreasing the FAR by a programmable low rate factor when the intrinsic atrial rate decreases. The rate smoothing filter further includes a safety feature for ensuring that the change in the FAR does not exceed the actual change in the intrinsic atrial rate. The safety feature works by setting the FAR equal to the intrinsic atrial rate of the current cycle if the intrinsic atrial rate of the current cycle did not change by as much as the high rate factor or the low rate factor.

The pacemaker of the present invention is typically programmed to operate primarily in a dual-chamber mode of operation, such as DDDR, where the heart is paced at a rate that follows or tracks the intrinsic atrial rate up to the maximum tracking rate (MTR) of the pacemaker. When the intrinsic atrial rate exceeds the MTR, the pacemaker stimulates the heart at or near the MTR, but also continues to monitor the FAR.

If the FAR exceeds a second upper rate limit (referred to as an atrial tachycardia detection rate (ATDR), a pathological atrial arrhythmia is deemed to exist, and the pacemaker automatically switches from its primary mode of operation to an alternate mode of operation (e.g., a non-atrial tracking or single-chamber mode of operation). Mode switching is performed to avoid pacing the ventricles at an undesirably high rate during periods of non-physiologic high atrial rates. Preferably, while in the alternate mode of operation, the pacemaker continues to monitor the FAR, and as soon as the FAR drops to the level of the MTR or below, the pacemaker automatically switches back to its primary atrial tracking mode.

The pacemaker of the present invention also includes the capability of switching from a primary set of operational parameter settings for the primary mode, to an alternate set of operational parameters for the alternate mode when the pacing mode is switched from the primary mode to the alternate mode. The pacemaker further includes the capability of returning to the primary set of operational parameter settings when the pacemaker switches back to the primary mode from the alternate mode. The settings are switched in order to optimize pacemaker performance in each mode. Typical operational parameters may include, but are not limited to, the base rate, the AV delay, the atrial and ventricular refractory periods, and the atrial and ventricular sense configurations. These parameters are initially set by the pacemaker manufacturer, but may be changed by a medical practitioner at the time of implantation or during the patient's follow-up visits.

The pacemaker of the present invention also includes the capability of recording and storing mode switching events and data pertaining to the mode switching events (e.g., such as the duration of the switch, the maximum FAR during the switch, etc.) in memory. The mode switching events and the associated data may be retrieved from the memory by a medical practitioner using an external programming system during a follow-up visit. This data may be important to the medical practitioner in determining if the pacemaker was performing properly under the previous mode switching criteria, or in deciding if a change in the mode switching criteria or other forms of patient therapy, such as antiarrhythmic drug therapy, is needed.

The present invention improves the performance of an automatic mode switching pacemaker and also improves the comfort of a patient by providing a rate smoothing filter for the sensed atrial rate and basing the mode switching decisions on the FAR. The present invention further improves the performance of the pacemaker by switching to a set of alternate pacemaker operational parameter settings that are optimized for a particular pacing settings when the pacemaker switches to that particular pacing mode. The present invention also improves the medical practitioner's decision-making ability by recording mode switching events and associated data in the pacemaker memory.

BRIEF DESCRIPTION OF THE DRAWINGS

The above and other advantages of the invention will be apparent upon consideration of the following detailed description, taken in conjunction with the accompanying drawings, in which like reference numerals refer to like parts throughout, and in which:

FIG. 1 is a block diagram of a mode switching pacemaker in accordance with the principles of the present invention;

FIG. 4 is a graph depicting the operation of the rate smoothing filter subroutine of FIG. 3 when the intrinsic atrial rate has increased since the previous cardiac cycle;

FIG. 5 is a graph depicting the operation of the rate smoothing filter subroutine of FIG. 3 when the intrinsic atrial rate has decreased since the previous cardiac cycle;

DETAILED DESCRIPTION OF THE PREFERRED EMBODIMENT

Figure 2:
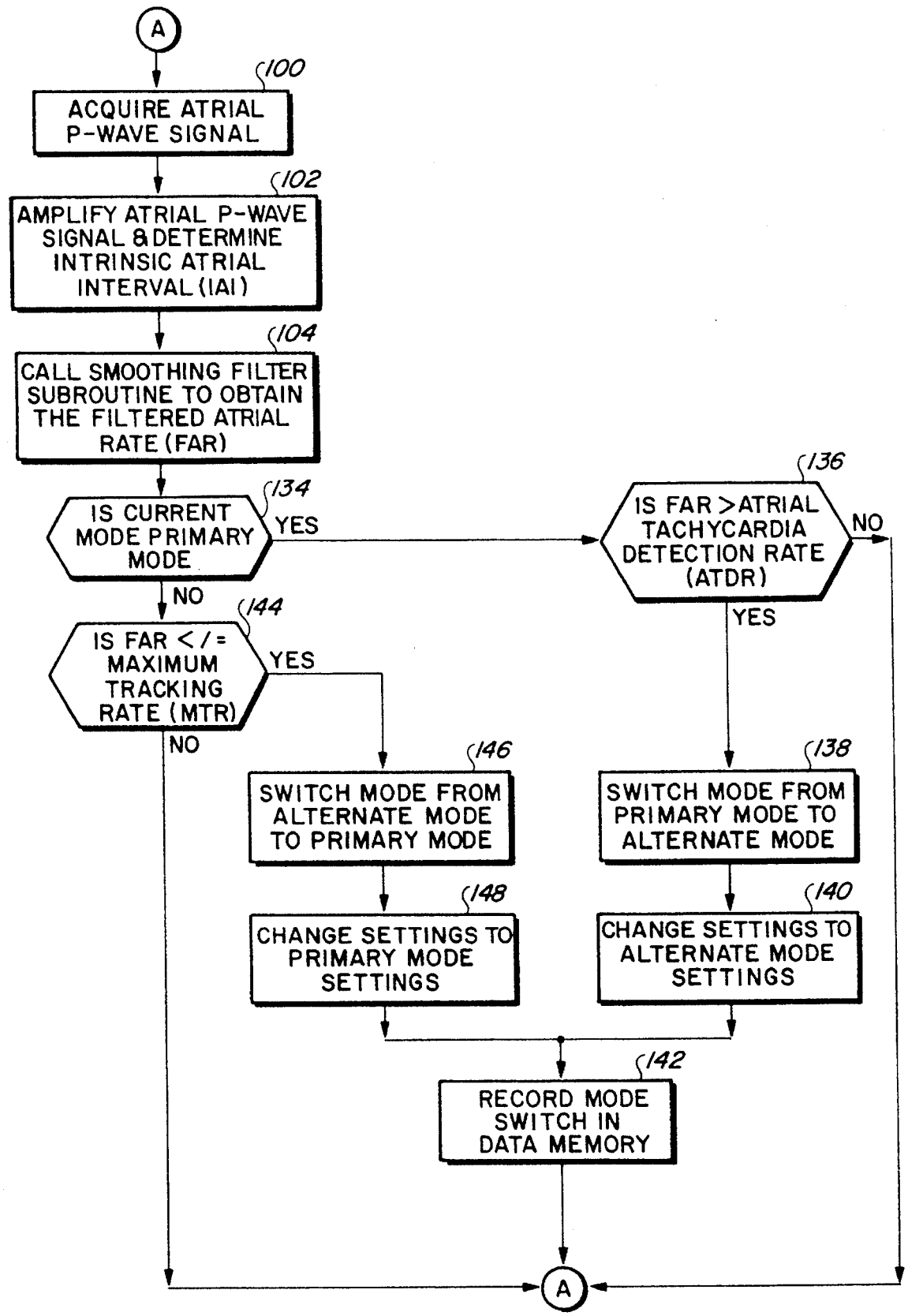
FIG. 2 depicts a logic flow diagram representing a control program executed by a microprocessor of the mode switching pacemaker shown in FIG. 1 in accordance with the principles of the present invention.

A pacemaker 10 in accordance with this invention is shown in FIG. 1. The pacemaker 10 is coupled to a heart 12 by way of leads 14 and 16, the lead 14 having an electrode 18 which is in contact with one of the atria of the heart 12, and the lead 16 having an electrode 20 which is in contact with one of the ventricles. The lead 14 carries stimulating pulses to the electrode 18 from an atrial pulse generator 22, while the lead 16 carries stimulating pulses to the electrode 20 from a ventricular pulse generator 24. In addition, electrical signals from the atria are carried from the electrode 18, through the lead 14 to the input terminal of an atrial sense amplifier 26. Electrical signals from the ventricles are carried from the electrode 20, through the lead 16 to the input terminal of a ventricular sense amplifier 28.

Controlling the dual-chamber pacemaker 10 is a control system 30. The control system 30 is preferably a microprocessor-based system such as the one disclosed in commonly assigned U.S. Pat. No. 4,940,052, entitled "Microprocessor Controlled Rate-Responsive Pacemaker Having Automatic Rate Response Threshold Adjustment," which is hereby incorporated by reference in its entirety. The control system 30 may also be a state logic-based system such as the one disclosed in the above-incorporated U.S. Pat. No. 4,944,298. The control system 30 also includes a real-time clock (not shown) for providing timing for monitoring cardiac events and for timing the application of therapeutic pulses by the pulse generators 22 and 24.

The control system 30 receives the output signals from the atrial amplifier 26 over a signal line 32. Similarly, the control system 30 receives the output signals from the ventricular amplifier 28 over a signal line 34. These output signals are generated each time that an atrial event (e.g., a P-wave) or a ventricular event (e.g., an R-wave) is sensed within the heart 12.

The control system 30 also generates an atrial trigger signal which is sent to the atrial pulse generator 22 over a signal line 36, and a ventricular trigger signal which is sent to the ventricular pulse generator 24 over a signal line 38. These trigger signals are generated each time that a stimulation pulse is to be generated by one of the pulse generators 22 or 24. The atrial stimulation pulse is referred to simply as the "A-pulse," and the ventricular stimulation pulse is referred to as the "V-pulse."

During the time that either an A-pulse or a V-pulse is being delivered to the heart 12, the corresponding atrial amplifier 26 or the ventricular amplifier 28 is typically disabled by way of a blanking signal presented to the appropriate amplifier from the control system 30 over a signal line 40 for the atrial amplifier 26 or a signal line 42 for the ventricular amplifier 28. This blanking action prevents the amplifiers 26 and 28 from becoming saturated with the relatively large stimulation pulses which are present at their input terminals during pacing pulse delivery. This blanking action also prevents residual electrical signals (known as "afterpotentials") present in the muscle tissue as a result of the pacemaker stimulation from being interpreted as atrial or ventricular events.

Still referring to FIG. 1, the pacemaker 10 also includes a memory circuit 44 which is coupled to the control system 30 through a suitable data bus 46. The memory circuit 44 allows certain control parameters used by the control system 30 in controlling the operation of the pacemaker 10 to be programmably stored and modified, as required, in order to customize the operation of the pacemaker 10 to suit the needs of a particular patient. In addition, data sensed during the operation of the pacemaker 10 (e.g., mode switching event data, as described below) may be stored in the memory circuit 44 for later retrieval and analysis.

A telemetry circuit 48 is further included in the pacemaker 10. The telemetry circuit 48 is connected to the control system 30 by way of a suitable command/data bus 50. In turn, the telemetry circuit 48 may be selectively coupled to an external programming device 52 by means of an appropriate communication link 54. The communication link 54 may be any suitable electromagnetic link such as an RF (radio frequency) channel.

Commands may be sent by the medical practitioner to the control system 30 from the external programmer 52 through the communication link 54. Similarly, through this communication link 54 and the external programmer 52, data (either held within the control system 30, as in a data latch, or stored within the memory circuit 44), may be remotely transmitted by the pacemaker 10 to the external programmer 52. In this manner, non-invasive communication may be established with the implanted pacemaker 10 from a remote, non-implanted location.

The operation of the pacemaker 10 is generally controlled by a control program stored in the memory circuit 44 and executed by the control system 30. This control program usually consists of multiple integrated program modules, with each module bearing responsibility for controlling one or more functions of the pacemaker 10. For example, one program module may control the delivery of stimulating pulses to the heart 12, while another module may control the acquisition of atrial and ventricular electrical signals. In effect, each program module is a control program dedicated to a specific function or a set of functions of the pacemaker 10.

Referring now to FIG. 2, a logic flow diagram representing an automatic mode switching control program ("control program") for the control system 30 of FIG. 1 in accordance with the present invention is described. This control program is executed in a loop, continuously providing the pacemaker 10 (FIG. 1) with the capability of distinguishing between a pathological arrhythmia and other conditions such as a normal sinus tachycardia or electrical noise. Preferably, one complete loop of the control program follows a single cardiac cycle. The control program also provides the pacemaker 10 (FIG. 1) with the capability of switching its mode from a primary atrial tracking mode to an alternate non-atrial tracking mode if a pathologic arrhythmia is detected, as well as the capability of switching back to the primary mode once the pathological arrhythmia subsides. Preferably, the mode switch may occur only once during a particular program cycle.

After the control program begins at a step 100, the control system 30 (FIG. 1) allows the pacemaker 10 (FIG. 1) to acquire a P-wave signal from the atria (not shown) of the heart 12 (FIG. 1) through the electrode 18 (FIG. 1). At a step 102, the control system 30 (FIG. 1) causes the atrial amplifier 26 (FIG. 1) to amplify the P-wave signal, and then receives the amplified P-wave signal through the signal line 32 (FIG. 1). At the step 102, the control system 30 (FIG. 1) also determines an intrinsic atrial interval (IAI) in milliseconds by measuring the interval between the P-wave sensed during the current cardiac cycle and the P-wave sensed during the previous cardiac cycle.

When the intrinsic atrial rate exceeds the MTR, the control system 30 (FIG. 1) begins ignoring certain P-waves occurring during pacemaker refractory periods for the purpose of maintaining AV synchrony. (The pacemaker refractory periods are programmable by the medical practitioner using the external programmer 52 (FIG. 1).) AV synchrony is maintained under these conditions by maintaining a relatively constant AV interval with respect to those P-waves that fall outside of the refractory periods. Since the P-waves occurring during the refractory periods are ignored for the purpose of maintaining AV synchrony, the control system 30 (FIG. 1) perceives an atrial rate that is lower than the intrinsic atrial rate. This lower atrial rate is referred to as the sensed functional atrial rate (SFAR). Thus, the control system 30 (FIG. 1) paces the ventricles at the SFAR, because pacing the ventricles at the intrinsic atrial rate exceeding a maximum tracking rate (MTR) set by the medical practitioner may be uncomfortable or dangerous to the patient. The MTR is typically the maximum rate at which the pacemaker 10 (FIG. 1) tracks the atrial rate when pacing the heart.

It is not desirable to base mode switching on the SFAR, because under certain conditions (such as 2:1 block where every other P-wave falls into the refractory period) the SFAR may be as low as one half of the intrinsic atrial rate, and thus an inaccurate indicator of actual atrial activity. For example, in a 2:1 block condition, the patient may be experiencing a tachycardia with the intrinsic atrial rate exceeding 200 bpm, while the SFAR would indicate 100 bpm since every other atrial beat is ignored. It is therefore preferable to base mode switching on an atrial rate representative of actual atrial activity. The intrinsic atrial rate, which is indicative of actual atrial activity, is derived when all P-waves, even the P-waves occurring during the refractory periods, are sensed by the control system 30 (FIG. 1).

Thus, to meet both objectives, the control system 30 (FIG. 1) determines the intrinsic atrial rate for the purpose of mode switching, and determines SFAR for the purpose of pacing by ignoring the P-waves occurring during the refractory periods. However, since the control system 30 (FIG. 1) is continuously sensing, its power requirements are increased.

Optionally, in pacemakers where power is limited, continuous atrial sensing may be initiated by a trigger. For example, continuous atrial sensing of the intrinsic atrial rate may be initiated if the intrinsic atrial rate exceeds a certain programmable trigger rate (PTR), the PTR preferably being less than the rate at which certain P-waves begin to be ignored by the control system 30 (FIG. 1). When the intrinsic atrial rate drops below the PTR, the continuous sensing of the intrinsic atrial rate would be disabled to conserve power.

The pacemaker 10 (FIG. 1) of the present invention has the capability of tracking the intrinsic atrial rate at a rate exceeding the set MTR. Thus, an atrial tachycardia detection rate (ATDR), which is higher than the MTR, may be programmed by the medical practitioner so that the heart may be paced at rates exceeding the MTR. The MTR is typically set at 80 to 180 beats per minute (bpm). The ATDR is programmable starting at 20 bpm above the MTR. This minimum 20 bpm gap allows the control system 30 (FIG. 1) to respond to pathologic arrhythmias when the intrinsic atrial rate reaches the ATDR, while avoiding responses based on slight atrial rate fluctuations above the MTR, but within the gap.

To avoid a response based on electrical noise or based on the atrial rate fluctuating above the ATDR and then below the MTR, the intrinsic atrial rate is preferably filtered.

At a step 104, the control system 30 (FIG. 1) calls a rate smoothing filter subroutine. Subroutines are known in the computer programming art as functions designed to perform specific tasks requested by a main program. One of the advantages of using subroutines is that two or more programs can use the same subroutine to perform a particular function. Modern programming techniques also encompass programmable "objects" which function similarly to subroutines. The main advantage of programmable "objects" is that once an "object" is developed to perform a particular function, it may be used in any program having a need to use that function. Thus, the rate smoothing filter subroutine may be used by the control system 30 (FIG. 1) for functions other than mode switching.

Figure 3:
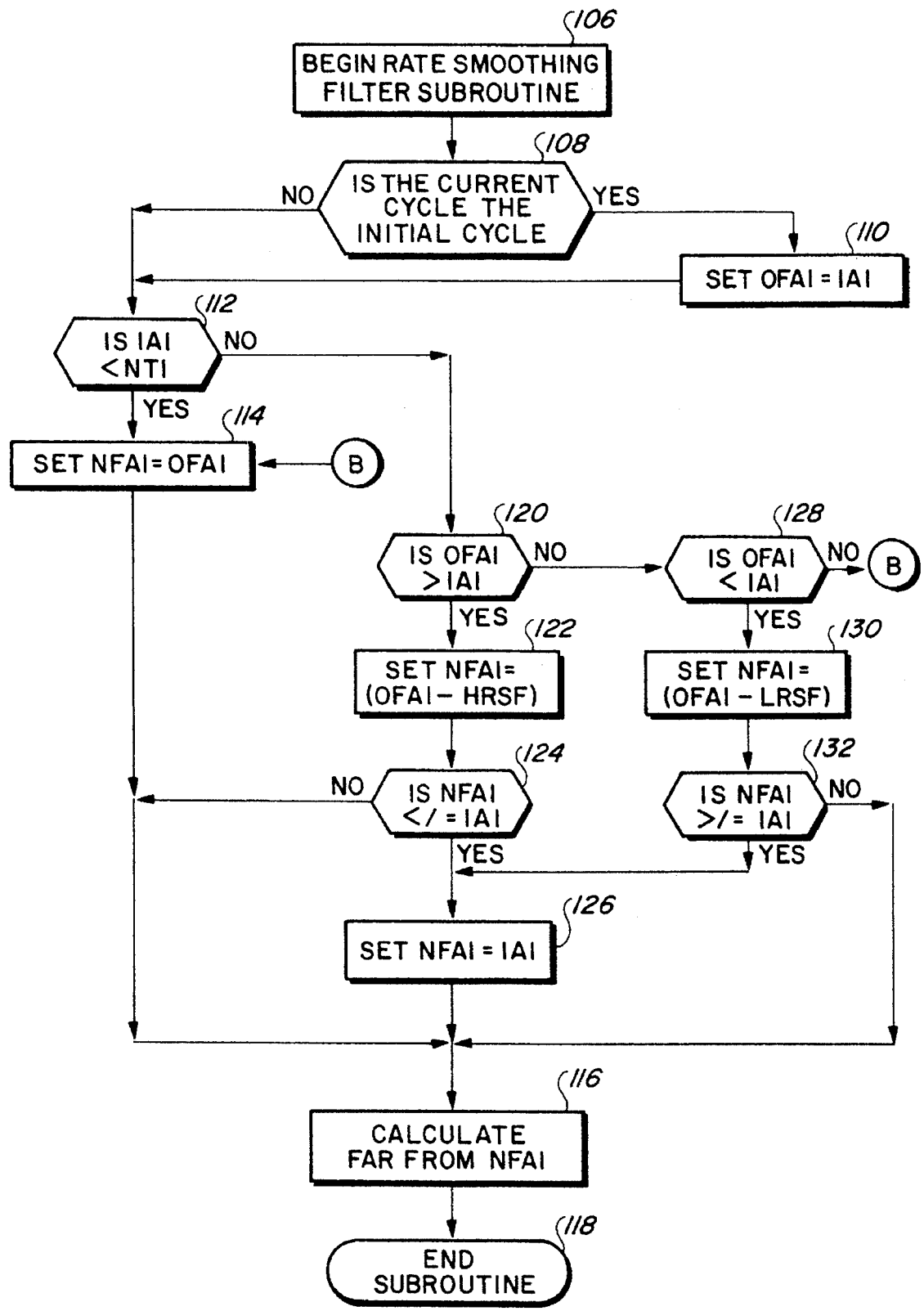
FIG. 3 depicts a logic flow diagram representing a rate smoothing filter subroutine executed by the microprocessor of the mode switching pacemaker shown in FIG. 1, for producing a filtered atrial rate in accordance with the principles of the present invention.

The rate smoothing filter subroutine ("subroutine"), shown in FIG. 3, filters the IAI determined at the step 102 (FIG. 2) to limit atrial rate fluctuations occurring from one cardiac cycle to the next, and to remove the influences of electrical noise. The control system 30 (FIG. 1) passes the IAI to the subroutine, and after executing the subroutine, derives a filtered atrial rate (FAR).

The subroutine operates on several intervals and factors which are measured in milliseconds. An interval in milliseconds is inversely proportional to the rate in beats per minute. The conversion between the interval and the corresponding rate is accomplished by dividing 60,000 by the interval to get the rate, or by dividing 60,000 by the rate to get the interval. For example, if the interval is 300 ms, the corresponding rate is 200 bpm.

Before describing the subroutine in greater detail it would be helpful to define the terminology of the various intervals and factors used in operation of the subroutine. An intrinsic atrial interval (IAI), as described above, is the atrial interval corresponding to the sensed intrinsic atrial rate of the current cycle determined by the control system 30 (FIG. 1) at the step 102 (FIG. 2). An "old" filtered atrial interval (OFAI) is the filtered atrial interval corresponding to the FAR of the previous cycle. Thus, if the FAR of the last cycle was 200 bpm, the OFAI of the current cycle would be 300 ms. A "new" filtered atrial interval (NFAI) is the filtered atrial interval corresponding to the FAR derived at the end of the current cycle. Thus if the NFAI is 400 ms, the FAR of the current cycle will be 150 bpm. A noise threshold interval (NTI) is the interval set by the medical practitioner to eliminate atrial fluctuations due to electrical noise and one-of-a-kind fast P-waves that occur at an interval less than the NTI. A high rate smoothing factor (HRSF) is a programmable constant which may be pre-set by the pacemaker manufacturer and later adjusted by the medical practitioner. The HRSF limits the amount by which the FAR may increase from the current cycle to the next cycle. Like the HRSF, a low rate smoothing factor (LRSF) is a programmable constant which may be pre-set by the pacemaker manufacturer and later adjusted by the medical practitioner. However, the LRSF limits the amount by which the FAR may decrease from the current cycle to the next cycle. The LRSF should be set lower than the HRSF because a higher FAR is preferable for the comfort of an active patient. Thus, the incremental increases in the FAR due to the HRSF are greater than the incremental decreases due to the LRSF.

The subroutine begins at a step 106. At a test 108, the control system 30 (FIG. 1) determines whether the current cycle is the initial cycle of the subroutine. The initial cycle of the subroutine is the first cycle after the pacemaker 10 (FIG. 1) begins its operation. For example, the medical practitioner may have reset the pacemaker 10 (FIG. 1) during a follow-up examination. If the control system 30 (FIG. 1) determines that the current cycle is the initial cycle, it proceeds to a step 110. At the step 110, the control system 30 (FIG. 1) sets the OFAI equal to the IAI. Thus, during the first cycle after start-up, the IAI is pre-loaded as the OFAI. If, at the test 108, the control system 30 (FIG. 1) determines that the current cycle is not the initial cycle, it proceeds to a test 112.

At the test 112 the control system 30 (FIG. 1) determines if the IAI is less than the NTI. The NTI may be programmed by the medical practitioner, but is preferably a low value such as 100 ms. For example, a IAI less than 100 ms indicates an atrial rate of over 600 beats per minute. Such a high rate would most likely be a result of electrical noise or a one-of-a-kind fast P-wave, and should be ignored. Thus, if the IAI is less than the NTI, the control system 30 (FIG. 1) proceeds to a step 114. At the step 114, the NFAI is set equal to the OFAI. At a step 116, the control system 30 (FIG. 1) calculates the FAR for the current cycle by dividing 60,000 by the NFAI to derive the FAR in beats per minute. At a step 118, the control system 30 (FIG. 1) ends the subroutine.

If at the test 112, the control system 30 (FIG. 1) determines that the IAI is not less than the NTI, the control system 30 (FIG. 1) proceeds to a test 120. At the test 120, the control system 30 (FIG. 1) determines whether the OFAI is greater than the IAI. If the OFAI is greater than the IAI, the control system 30 (FIG. 1) proceeds to a step 122. At the step 122 the control system 30 (FIG. 1) derives the NFAI by subtracting the HRSF from the OFAI. The HRSF is preferably set at approximately 38 ms.

Referring briefly to FIG. 4, an example is provided showing the effect of the subroutine when the OFAI is 400 ms (the FAR of the last cycle is 150 bpm) and the IAI has decreased to 300 ms (i.e., the intrinsic atrial rate has increased to 200 bpm). At the step 122 (FIG. 3), the NFAI is set at 362 ms (resulting in the FAR of 166 bpm), since 400 ms (OFAI) minus 38 ms (HRSF) equals 362 ms. Thus, instead of the FAR jumping from 150 bpm to 200 bpm from one cycle to the next, the FAR only increases from 150 bpm to 166 bpm in the span of one cycle. The medical practitioner may adjust the HRSF to provide a smaller or greater increment for increases in the FAR with each cycle.

Returning now to FIG. 3, at a test 124 the control system 30 (FIG. 1) determines if the NFAI obtained at the step 122 is less than or equal to the IAI. This test ensures that if the IAI dropped by a lesser amount than the HRSF, the decrease in the NFAI is limited by the amount of the actual drop in the IAI. For example if the OFAI is 400 ms (the FAR of the last cycle is 150 bpm) and the IAI decreases to 380 ms (i.e., the intrinsic atrial rate increases to 158 bpm) since the last cycle, subtracting 38 ms (HRSF) from 400 ms (OFAI) would be inappropriate because doing so would set the NFAI at 362 ms. A NFAI value of 362 ms would result in the FAR equal to 166 bpm, exceeding the intrinsic atrial rate of 158 bpm.

This potential problem is avoided at the test 124 by comparing the NFAI obtained at the step 122 to the IAI. If the NFAI is less than or equal to the IAI, then at a step 126, the NFAI is set equal to the IAI. Thus, returning to the above example, if the OFAI is 400 ms, and the IAI is 380 ms, at the step 122, the NFAI is set at 362 ms, exceeding the actual drop in the IAI. However, at the step 126, the NFAI is set equal to 380 ms—the IAI. The above procedure ensures that the NFAI is never less than the IAI if the magnitude of the decrease in IAI is less than the HRSF.

After the step 126, the control system 30 (FIG. 1) proceeds to the step 116 where the control system 30 (FIG. 1) calculates the FAR from the NFAI, and then proceeds to the step 118, where the control system 30 (FIG. 1) ends the subroutine. If, at the step 124, the control system 30 (FIG. 1) determines that the NFAI is not greater than or equal to the IAI, the control system 30 (FIG. 1) proceeds to the step 116 where the control system 30 (FIG. 1) calculates the FAR from the NFAI, and then proceeds to the step 118, where it ends the subroutine.

If, at the test 120, the control system 30 (FIG. 1) determines that the OFAI is not greater than the IAI, the control system 30 (FIG. 1) proceeds to a test 128. At the test 128, the control system 30 (FIG. 1) determines whether the OFAI is less than the IAI. If, at the test 128, the control system 30 (FIG. 1) determines that the OFAI is not less than the IAI, the control system 30 (FIG. 1) proceeds to the step 114 where the NFAI is set equal to the OFAI. Thus, if the current value of IAI is the same as the OFAI from the last cycle, the FAR will not change in this cycle. The control system 30 (FIG. 1) then proceeds to the step 116 where the control system 30 (FIG. 1) calculates the FAR from the NFAI, and then proceeds to the step 118, where it ends the subroutine.

If, at the test 128, the control system 30 (FIG. 1) determines that the OFAI is less than the IAI, the control system 30 (FIG. 1) proceeds to a step 130. At the step 130, the control system 30 (FIG. 1) determines the NFAI by adding the LRSF to the OFAI. The LRSF is preferably set at approximately 25 ms.

Referring briefly to FIG. 5, an example is provided showing the effect of the subroutine when the OFAI is 300 ms (the FAR of the last cycle is 200 bpm) and the IAI has increased to 400 ms (i.e., the intrinsic atrial rate has decreased to 150 bpm). At the step 130 (FIG. 3), the NFAI is set at 325 ms (resulting in the FAR of 166 bpm), since 300 ms (OFAI) plus 25 ms (LRSF) equals 325 ms. Thus, instead of the FAR dropping from 200 bpm to 150 bpm from one cycle to the next, the FAR only decreases from 200 bpm to 185 bpm in the span of one cycle. The medical practitioner may adjust the LRSF to provide smaller or greater increments for the drop in the FAR with each cycle, however as explained above, the LRSF should be set lower than the HRSF.

Returning now to FIG. 3, at a test 132 the control system 30 (FIG. 1) determines if the NFAI obtained at the step 130 is greater than or equal to the IAI. This test ensures that if the IAI increased by a lesser amount than the LRSF, the increase in the NFAI is limited by the amount of the actual increase in the IAI. For example, if the OFAI is 380 ms (the FAR of the last cycle is 158 bpm) and the IAI increases to 390 ms (i.e., the intrinsic atrial rate decreases to 154 bpm) since the last cycle, adding 25 ms (LRSF) to 380 ms (OFAI) would be inappropriate because doing so would set the NFAI at 405 ms. An NFAI value of 405 ms would result in the FAR equal to 148 bpm, lower than the intrinsic atrial rate of 154 bpm.

This potential problem is avoided by comparing the NFAI obtained at the step 130 to the IAI. If the NFAI is greater than or equal to the IAI, the control system 30 (FIG. 1) proceeds to the step 126, where the NFAI is set equal to the IAI. Thus, returning to the above example, if the OFAI is 380 ms, and the IAI is 390 ms, at the step 130, the NFAI is set at 405 ms, exceeding the actual drop in the IAI. However, at the step 126, the NFAI is set equal to 390 ms—the IAI. The above procedure ensures that the NFAI is never greater than the IAI if the increase in IAI is less than the LRSF. After the step 126 the control system 30 (FIG. 1) proceeds to the step 116 where the control system 30 (FIG. 1) calculates the FAR from the NFAI, and then proceeds to the step 118, where it ends the subroutine.

If, at the step 132, the control system 30 (FIG. 1) determines that the NFAI is not less than or equal to the IAI, the control system 30 (FIG. 1) proceeds to the step 116 where the control system 30 (FIG. 1) calculates the FAR from the NFAI, and then proceeds to the step 118, where it ends the subroutine.

Returning now to FIG. 2, at a test 134, the control system 30 (FIG. 1) determines if the pacemaker 10 (FIG. 1) is currently in a primary mode of operation by checking if a primary mode program "flag" is active. The program "flag" may be a value in one of the program memory areas of the memory 44 (FIG. 1). The primary mode of operation is preferably an atrial tracking mode.

If, at the test 134, the control system 30 (FIG. 1) determines that the pacemaker 10 (FIG. 1) is currently in the primary mode of operation, the control system 30 (FIG. 1) proceeds to a test 136. At the test 136, the control system 30 (FIG. 1) determines if the FAR determined using the rate smoothing filter subroutine of FIG. 3 is greater than the ATDR. If the FAR is greater than the ATDR, a pathologic arrhythmia (e.g., atrial tachycardia, fibrillation, or flutter) is most likely occurring. The program then proceeds to a step 138, at which the control system 30 (FIG. 1) acts to terminate atrial tracking ventricular pacing by switching the pacemaker 10 (FIG. 1) from the primary atrial tracking mode of operation to an alternate non-atrial tracking mode. The alternate mode may be any suitable non-atrial tracking mode, but is preferably a single-chamber ventricular mode such as VVIR, which only tracks and paces the ventricles in accordance with physiologic need. At the step 138, the control system 30 (FIG. 1) also deactivates the primary mode program "flag."

At a step 140, the control system 30 (FIG. 1) advantageously changes the operational parameters from settings appropriate for the primary mode to settings appropriate to the alternate mode. Since the primary operational parameter settings are usually optimized for performance in the primary mode, it is desirable to switch the settings to the alternate operational parameter settings when the mode is switched from primary mode to the alternate mode at the step 138. The medical practitioner may define a set of alternate operational parameter settings for the alternate mode in order to optimize the performance of the pacemaker 10 (FIG. 1) when the mode is switched from the primary mode to the alternate mode. For example, if during an atrial arrhythmia the control system 30 (FIG. 1) changes to a VVIR mode at the step 138, a higher base rate setting associated with the VVIR mode may enhance cardiac performance that has been adversely affected by loss of AV synchrony. The set of alternate operational parameters may include, but is not limited to, the base rate, the ventricular pulse width, the atrial and ventricular refractory periods, and the atrial and ventricular sense configurations.

Figure 6:
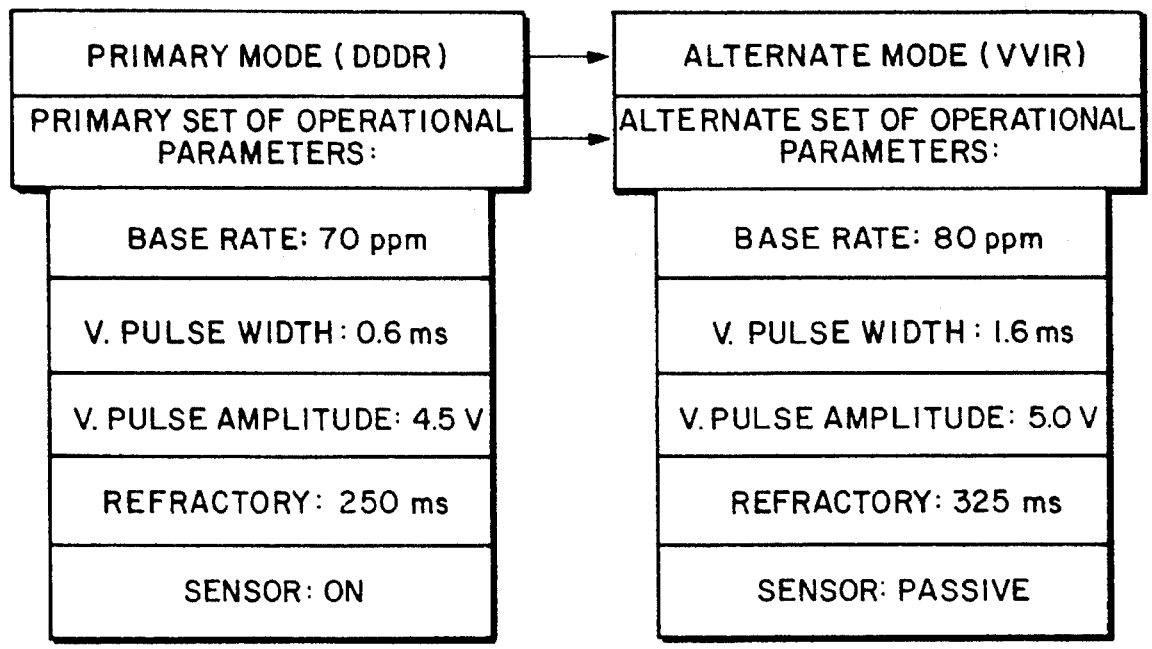
FIG. 6 is a table containing an example of a primary set of operational parameters for use by the mode switching pacemaker of FIG. 1 when the pacemaker is in a primary mode of operation, and an example of an alternate set of operational parameters for use by the mode switching pacemaker of FIG. 1 when the pacemaker is in an alternate mode of operation in accordance with the principles of the present invention.

Referring now to FIG. 6, illustrative primary and alternate operational parameter settings are described. The primary operational parameter settings in the above example include a base rate set at 70 pulses per minute (ppm), a ventricular pulse width of 0.6 ms, a ventricular pulse amplitude of 4.5 V, a refractory period of 250 ms, and an active sensor. The alternate operational parameter settings in the above example include a base rate set at 80 ppm, a ventricular pulse width of 1.6 ms, a ventricular pulse amplitude of 5.0 V, a refractory period of 325 ms, and a passive sensor. Of course, one of ordinary skill in the art could implement primary and alternate operational parameter settings in accordance with the principles of the present invention without necessarily providing the rate-smoothing filter described above in connection with FIG. 2.

Returning now to FIG. 2, at a step 142, the control system 30 (FIG. 1) records the mode switch event of the step 138, along with associated data, into the memory circuit 44 (FIG. 1). The recorded associated data may include, but are not limited to, the maximum FAR achieved during the mode switch, the duration of the mode switch, and the time and date of the switch.

Figure 7:
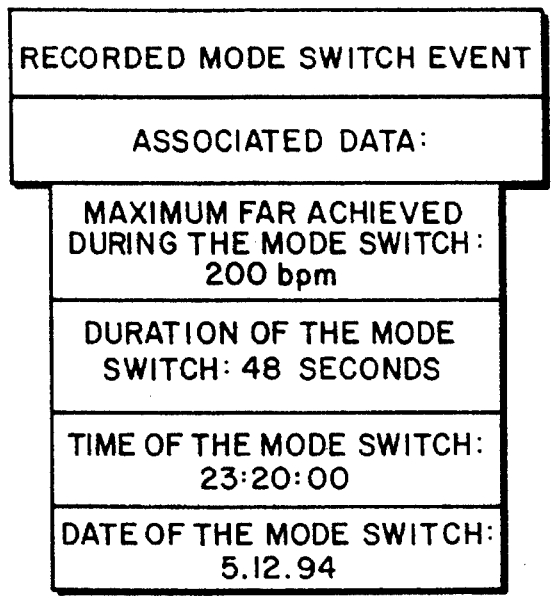
FIG. 7 is a table containing an illustrative list of data items pertaining to mode switching events that may be recorded by the mode switching pacemaker of FIG. 1 when mode switching occurs in accordance with the principles of the present invention.

Referring briefly to FIG. 7, an example of data that may be associated with a mode switch are illustrated. In this example, the maximum FAR achieved during the mode switch was 200 bpm, the duration of the mode switch was 48 seconds, the time of the switch was 23:20:00 (11:20 PM) and date of the switch was Jan. 1, 1999.

In most pacemakers, the memory circuit 44 (FIG. 1) is of limited size; therefore, the medical practitioner is given several options for determining how the mode switching data are stored. For example, a circular buffer in the memory circuit 44 may be used. A circular buffer stores a fixed amount of data, and discards a proportional amount of old data when a certain amount of new data is received. Thus, if the circular buffer has the capability of storing five mode switching events, and five events have been recorded, the sixth event causes the first event record to be erased, and so on. This approach is useful if the medical practitioner is interested in seeing the most recent mode switching events before the follow-up examination.

However, if the medical practitioner is interested in evaluating the mode switching events occurring immediately after the most recent follow-up examination, a static memory area defined in the memory circuit 44 (FIG. 1) may be used. A static memory area can store mode switching data until the memory area is filled up, whereupon recording of data stops. Thus, if the static memory area has the capability of storing five mode switching events, and five events have been recorded, the sixth event is not recorded because the static memory area would be filled. Of course, if sufficient memory is present, the control system 30 (FIG. 1) records all mode switching events which occur. The mode switching data may be retrieved by the medical practitioner from the memory circuit 44 (FIG. 1) during a follow-up examination using the external programming system 52 (FIG. 1). The external programming system 52 (FIG. 1) may compile the mode switching data into reports which may aid the medical practitioner in determining if the pacemaker is operating properly. The reports may also aid the medical practitioner in deciding whether adjustment is necessary in mode switching criteria, such as the MTR and the ATDR, and in the filter values, such as the HRSF and the LRSF. Of course, the mode switching data recording function and the data storage schemes described above may be used in any conventional mode switching pacemaker without departing from the spirit of this invention.

Returning now to FIG. 2, the control system 30 (FIG. 1) completes the loop by returning to the step 100 for the next cardiac cycle. If, at the test 134, the control system 30 (FIG. 1) determines that the pacemaker 10 (FIG. 1) is not currently in the primary mode of operation, the control system 30 (FIG. 1) proceeds to a test 144. At the test 144, the control system 30 (FIG. 1) determines if the FAR obtained from the rate smoothing filter subroutine of FIG. 3, is less than or equal to the MTR. If the FAR is not less than or equal to the MTR, the control system 30 (FIG. 1) returns to the step 100.

If, on the other hand, the FAR is less than or equal to the MTR, the control system 30 (FIG. 1) proceeds to a step 146. At the step 146, the control system 30 (FIG. 1) switches the mode of operation of the pacemaker 10 (FIG. 1) from the alternate mode to the primary mode. The MTR is set as the criteria for switching back to the primary mode in order to enable the primary mode to be dominant and thus maintain A-V synchrony even at a high pacing rate. This criteria is particularly beneficial to patients with normally high atrial rates. Switching to the primary mode when the FAR falls below the MTR advantageously avoids frequent mode switching, which may occur when identical thresholds for switching to and from the primary mode are used. At the step 146, the control system 30 (FIG. 1) also activates the primary mode program "flag."

At a step 148, the control system 30 (FIG. 1) changes the operational parameters from the alternate mode settings to the primary mode settings. Since the primary operational parameter settings are usually optimized for performance in the primary mode, it is desirable to switch the settings to the primary operational parameter settings when the mode is switched from alternate mode to the primary mode at the step 146.

The program then proceeds to the step 142 where the control system 30 (FIG. 1) records the mode switch event of the step 146, along with associated data, into the memory circuit 44 (FIG. 1). The recorded data may include, but are not limited to, the maximum FAR achieved during the mode switch, the duration of the mode switch, the variance of individual atrial and ventricular events during the mode switch (to indicate the type of pathologic arrhythmia triggering the mode switch), and the time and date of the switch. The control system 30 (FIG. 1) then returns to the step 100.

Thus, an implantable dual-chamber pacemaker programmed to operate primarily in an atrial tracking mode is provided, where the pacemaker includes an atrial rate smoothing filter for producing a filtered atrial rate from an intrinsic atrial rate, and where the pacemaker automatically switches its mode of operation from the atrial tracking mode to a non-atrial tracking mode in the event the filtered atrial rate exceeds a prescribed upper rate limit. The pacemaker switches from a primary set of operational parameter settings for the primary mode, to an alternate set of operational parameters for the alternate mode when the mode is switched from the primary mode to the alternate mode. The pacemaker also includes the capability of recording and storing mode switching events and data pertaining to the mode switching events.

One skilled in the art will appreciate that the present invention can be practiced by other than the described embodiments, which are presented for purposes of illustration and not of limitation, and the present invention is limited only by the claims that follow.

What is claimed is:

1. An implantable pacemaker comprising:

first and second leads adapted to couple the pacemaker to, respectively, an atrial chamber and a ventricular chamber of a heart;

atrial sense circuitry for sensing an intrinsic atrial rate through the first lead;

pulse generating circuitry for generating pacing pulses for delivery to the atrial and ventricular chambers through, respectively, the first and second leads; and a control system, coupled to the atrial sense circuitry and the pulse generating circuitry, for deriving during each cardiac cycle, from the intrinsic atrial rate, a filtered atrial rate that exhibits less variation between successive cardiac cycles than the intrinsic atrial rate, for causing the pulse generating circuitry to generate pacing pulses in accordance with a primary mode of operation when the filtered atrial rate is less than a first threshold rate, for causing the pulse generating circuitry to generate pacing pulses in accordance with an alternate mode of operation when the filtered atrial rate exceeds the first threshold rate, the control system in the alternate mode of operation, causing the pulse generating circuitry to again generate pacing pulses in accordance with the primary mode when the filtered atrial rate falls below a second threshold rate.

2. The pacemaker of claim 1, wherein the control system derives the filtered atrial rate by limiting increases in the filtered atrial rate between successive cardiac cycles and by limiting decreases in the filtered atrial rate between successive cardiac cycles.

3. The pacemaker of claim 2, wherein to limit increases in the filtered atrial rate between successive cardiac cycles, the control system increments the filtered atrial rate derived for a cardiac cycle immediately preceding a current cardiac cycle by a first rate limiting factor to derive the filtered atrial rate for the current cardiac cycle when the intrinsic atrial rate sensed for the current cardiac cycle exceeds the filtered atrial rate derived for the preceding cardiac cycle.

4. The pacemaker of claim 3, wherein the control system sets the filtered atrial rate for the current cardiac cycle equal to the intrinsic atrial rate for the current cardiac cycle when the filtered atrial rate derived by incrementing the filtered atrial rate derived for the preceding cardiac cycle exceeds the intrinsic atrial rate for the current cardiac cycle.

5. The pacemaker of claim 3, wherein the control system sets the filtered atrial rate for the current cardiac cycle equal to the filtered atrial rate derived for the preceding cardiac cycle when the intrinsic atrial rate for the current cardiac cycle exceeds a noise threshold rate that is significantly greater than the first threshold rate.

6. The pacemaker of claim 3, wherein to limit decreases in the filtered atrial rate between successive cardiac cycles, the control system decrements the filtered atrial rate derived for the preceding cardiac cycle by a second rate limiting factor to derive the filtered atrial rate for the current cardiac cycle when the intrinsic atrial rate sensed for the current cardiac cycle is less than the filtered atrial rate derived for the preceding cardiac cycle.

7. The pacemaker of claim 6, wherein the control system sets the filtered atrial rate for the current cardiac cycle equal to the intrinsic atrial rate for the current cardiac cycle when the filtered atrial rate derived by decrementing the filtered atrial rate derived for the previous cardiac cycle is less than the intrinsic atrial rate for the current cardiac cycle.

8. The pacemaker of claim 6, wherein the second rate limiting factor is less than the first rate limiting factor.

9. The pacemaker of claim 1, wherein:
in the primary mode of operation, the control system causes the pulse generating circuitry to generate pacing pulses in accordance with a primary set of operational parameters;
in the alternate mode of operation, the control system causes the pulse generating circuitry to generate pacing pulses in accordance with an alternate set of operational parameters; and
the control system switches from the primary set of operational parameters to the alternate set of operational parameters when the filtered atrial rate exceeds the first threshold rate.

10. The pacemaker of claim 1, further comprising a memory, wherein the control system stores data pertaining to the change in the mode of operation in the memory when the mode of operation switches from the primary mode to the alternate mode.

11. The pacemaker of claim 1, wherein the primary mode is an atrial tracking mode and the alternate mode is a non-atrial tracking mode.

12. An implantable pacemaker having a plurality of programmably selectable modes of operation including a primary mode and an alternate mode, the pacemaker having atrial sensing means for sensing an intrinsic atrial rate in an atrial chamber of a heart, the pacemaker comprising:
filtering means for deriving during each cardiac cycle, from the intrinsic atrial rate, a filtered atrial rate that exhibits less variation between successive cardiac cycles than the intrinsic atrial rate;
monitoring means for determining when the filtered atrial rate exceeds a first threshold rate, and also for determining, when the pacemaker is operating in the alternate mode, when the filtered atrial rate falls below a second threshold rate that is less than the first threshold rate; and
mode switching means for changing the mode of operation from the primary mode to the alternate mode when the monitoring means determines that the filtered atrial rate exceeds the first threshold rate, and for changing the mode of operation from the alternate mode to the primary mode when the monitoring means determines that the filtered atrial rate falls below a second threshold rate.

13. The pacemaker of claim 12, wherein the filtering means comprises:
first limiting means for limiting increases in the filtered atrial rate between successive cardiac cycles; and
second limiting means for limiting decreases in the filtered atrial rate between successive cardiac cycles.

14. The pacemaker of claim 13, wherein the first limiting means comprises means for incrementing the filtered atrial rate derived for a cardiac cycle immediately preceding a current cardiac cycle by a first rate limiting factor to derive the filtered atrial rate for the current cardiac cycle when the intrinsic atrial rate sensed for the current cardiac cycle exceeds the filtered atrial rate derived for the preceding cardiac cycle.

15. The pacemaker of claim 14, wherein the first limiting means further comprises means for setting the filtered atrial rate for the current cardiac cycle equal to the intrinsic atrial rate for the current cardiac cycle when the filtered atrial rate derived by the means for incrementing exceeds the intrinsic atrial rate for the current cardiac cycle.

16. The pacemaker of claim 14, wherein the first limiting means further comprises means for setting the filtered atrial rate for the current cardiac cycle equal to the filtered atrial rate derived for the preceding cardiac cycle when the intrinsic atrial rate for the current cardiac cycle exceeds a noise threshold rate that is significantly greater than the first threshold rate.

17. The pacemaker of claim 14, wherein the second limiting means comprises means for decrementing the filtered atrial rate derived for the preceding cardiac cycle by a second rate limiting factor to derive the filtered atrial rate for the current cardiac cycle when the intrinsic atrial rate sensed for the current cardiac cycle is less than the filtered atrial rate derived for the preceding cardiac cycle.

18. The pacemaker of claim 17, wherein the second limiting means further comprises means for setting the filtered atrial rate for the current cardiac cycle equal to the intrinsic atrial rate for the current cardiac cycle when the filtered atrial rate derived by the means for decrementing is less than the intrinsic atrial rate for the current cardiac cycle.

19. The pacemaker of claim 17, wherein the second rate limiting factor is less than the first rate limiting factor.

20. The pacemaker of claim 12, wherein:

the primary mode is associated with a primary set of operational parameters defining the operation of the pacemaker in the primary mode;

the alternate mode is associated with an alternate set of operational parameters defining the operation of the pacemaker in the alternate mode; and the pacemaker further comprises parameter switching means for switching from the primary set of operational parameters to the alternate set of operational parameters when the mode switching means switches from the primary mode to the alternate mode.

21. The pacemaker of claim 12, further comprising recording means for recording data pertaining to the change in the mode of operation when the mode switching means switches the mode of operation from the primary mode to the alternate mode.

22. The pacemaker of claim 12, wherein the primary mode is an atrial tracking mode and the alternate mode is a non-atrial tracking mode.

23. A method of operating an implantable pacemaker having a plurality of programmably selectable modes of operation including a primary mode and an alternate mode, the pacemaker having atrial sensing circuitry for sensing an intrinsic atrial rate in an atrial chamber of a heart, the method comprising the steps of:

deriving during each cardiac cycle, from the intrinsic atrial rate, a filtered atrial rate that exhibits less variation between successive cardiac cycles than the intrinsic atrial rate;

determining when the filtered atrial rate exceeds a first threshold rate;

changing the mode of operation from the primary mode to the alternate mode when the filtered atrial rate exceeds the first threshold rate;

determining, when the pacemaker is operating in the alternate mode, when the filtered atrial rate falls below a second threshold rate that is less than the first threshold rate; and changing the mode of operation from the alternate mode to the primary mode when the filtered atrial rate falls below the second threshold rate.

24. The method of claim 23, wherein the filtering step comprises the steps of:

limiting increases in the filtered atrial rate between successive cardiac cycles; and limiting decreases in the filtered atrial rate between successive cardiac cycles.

25. The method of claim 24, wherein the step of limiting increases comprises the step of incrementing the filtered atrial rate derived for a cardiac cycle immediately preceding a current cardiac cycle by a first rate limiting factor to derive the filtered atrial rate for the current cardiac cycle when the intrinsic atrial rate sensed for the current cardiac cycle exceeds the filtered atrial rate derived for the preceding cardiac cycle.

26. The method of claim 25, wherein the step of limiting increases further comprises the step of setting the filtered atrial rate for the current cardiac cycle equal to the intrinsic atrial rate for the current cardiac cycle when the filtered atrial rate derived in the incrementing step exceeds the intrinsic atrial rate for the current cardiac cycle.

27. The method of claim 25, wherein the step of limiting increases further comprises the step of setting the filtered atrial rate for the current cardiac cycle equal to the filtered atrial rate derived for the preceding cardiac cycle when the intrinsic atrial rate for the current cardiac cycle exceeds a noise threshold rate that is significantly greater than the first threshold rate.

28. The method of claim 25, wherein the step of limiting decreases comprises the step of decrementing the filtered atrial rate derived for the preceding cardiac cycle by a second rate limiting factor to derive the filtered atrial rate for the current cardiac cycle when the intrinsic atrial rate sensed for the current cardiac cycle is less than the filtered atrial rate derived for the preceding cardiac cycle.

29. The method of claim 28, wherein the step of limiting decreases further comprises the step of setting the filtered atrial rate for the current cardiac cycle equal to the intrinsic atrial rate for the current cardiac cycle when the filtered atrial rate derived in the decrementing step is less than the intrinsic atrial rate for the current cardiac cycle.

30. The method of claim 28, wherein the step of decrementing the filtered atrial rate comprises a step of decrementing the filtered atrial rate derived for the preceding cardiac cycle by a second rate limiting factor, the second rate limiting factor being less than the first rate limiting factor.

31. The method of claim 23, wherein:

the primary mode is associated with a primary set of operational parameters defining the operation of the pacemaker in the primary mode;

the alternate mode is associated with an alternate set of operational parameters defining the operation of the pacemaker in the alternate mode; and the changing step comprises the step of switching from the primary set of operational parameters to the alternate set of operational parameters when the mode is switched from the primary mode to the alternate mode.

32. The method of claim 23, further comprising the step of recording data pertaining to the change in the mode of operation when the mode of operation is changed from the primary mode to the alternate mode.

33. The method of claim 23, wherein the step of changing the mode of operation from the primary mode to the alternate mode comprises changing the mode of operation from an atrial tracking mode to a non-atrial tracking mode.

34. An implantable pacemaker having a plurality of programmably selectable modes of operation including a primary mode and an alternate mode, the pacemaker having atrial sensing means for sensing an intrinsic atrial rate in an atrial chamber of a heart, the pacemaker comprising:

filtering means for deriving, from the intrinsic atrial rate, a filtered atrial rate that exhibits less variation between successive cardiac cycles than the intrinsic atrial rate, wherein the filtering means comprises:

first limiting means for limiting increases in the filtered atrial rate between successive cardiac cycles comprising means for setting the filtered atrial rate for the current cardiac cycle equal to the intrinsic atrial rate for the current cardiac cycle when the filtered atrial rate derived by the filtering means exceeds the intrinsic atrial rate for the current cardiac cycle, and second limiting means for limiting decreases in the filtered atrial rate between successive cardiac cycles comprising means for setting the filtered atrial rate for the current cardiac cycle equal to the intrinsic atrial rate for the current cardiac cycle when the filtered atrial rate derived by the filtering means is less than the intrinsic atrial rate for the current cardiac cycle;

monitoring means for determining when the filtered atrial rate exceeds a first threshold rate; and mode switching means for changing the mode of operation from the primary mode to the alternate mode when the monitoring means determines that the filtered atrial rate exceeds the first threshold rate.

35. An implantable pacemaker having a plurality of programmably selectable modes of operation including a primary mode and an alternate mode, the pacemaker having atrial sensing means for sensing an intrinsic atrial rate in an atrial chamber of a heart, the pacemaker comprising:

filtering means for deriving, from the intrinsic atrial rate, a filtered atrial rate that exhibits less variation between successive cardiac cycles than the intrinsic atrial rate;

monitoring means for determining when the filtered atrial rate exceeds a first threshold rate;

mode switching means for changing the mode of operation from the primary mode to the alternate mode when the monitoring means determines that the filtered atrial rate exceeds the first threshold rate; and recording means for recording data pertaining to the change in the mode of operation when the mode switching means switches the mode of operation from the primary mode to the alternate mode.

* * * * *